United States Patent
Zelnik et al.

(10) Patent No.: US 7,639,782 B2
(45) Date of Patent: Dec. 29, 2009

(54) METHODS AND SYSTEMS FOR AUTOMATIC PATIENT TABLE POSITIONING

(75) Inventors: Deborah Ruth Zelnik, Haifa (IL); Pascal Salazar-ferrer, Minneapolis, MN (US)

(73) Assignee: GE Medical Systems Israel, Ltd., Tel Aviv (IL)

( * ) Notice: Subject to any disclaimer, the term of this patent is extended or adjusted under 35 U.S.C. 154(b) by 280 days.

(21) Appl. No.: 11/484,297

(22) Filed: Jul. 11, 2006

(65) Prior Publication Data

US 2007/0053503 A1 Mar. 8, 2007

Related U.S. Application Data

(60) Provisional application No. 60/710,393, filed on Aug. 23, 2005.

(51) Int. Cl.
*A61B 6/04* (2006.01)
*G01N 23/04* (2006.01)
(52) U.S. Cl. .................... 378/62; 378/20; 378/195; 378/196; 600/407; 600/425
(58) Field of Classification Search .............. 378/20, 378/62, 63, 162, 165, 195, 196, 198, 209; 600/407, 425
See application file for complete search history.

(56) References Cited

U.S. PATENT DOCUMENTS

| | | | | |
|---|---|---|---|---|
| 5,124,337 A | * | 6/1992 | Dugar et al. | 514/307 |
| 5,797,849 A | | 8/1998 | Vesely et al. | |
| 6,110,109 A | * | 8/2000 | Hu et al. | 600/300 |
| 6,246,898 B1 | | 6/2001 | Vesely et al. | |
| 6,385,283 B1 | * | 5/2002 | Stein et al. | 378/54 |
| 6,463,121 B1 | * | 10/2002 | Milnes | 378/62 |
| 6,522,712 B1 | * | 2/2003 | Yavuz et al. | 378/4 |
| 6,785,410 B2 | * | 8/2004 | Vining et al. | 382/128 |
| 6,816,603 B2 | | 11/2004 | David et al. | |
| 7,412,029 B2 | * | 8/2008 | Myles | 378/65 |
| 2004/0254439 A1 | | 12/2004 | Fowkes et al. | |
| 2005/0059873 A1 | | 3/2005 | Glozman et al. | |
| 2005/0070781 A1 | | 3/2005 | Dawant et al. | |
| 2005/0197655 A1 | | 9/2005 | Telfair et al. | |
| 2005/0283070 A1 | | 12/2005 | Imielinska et al. | |
| 2006/0079759 A1 | | 4/2006 | Vaillant et al. | |
| 2007/0081630 A1 | * | 4/2007 | Evron | 378/108 |

* cited by examiner

*Primary Examiner*—Allen C. Ho
(74) *Attorney, Agent, or Firm*—Dean Small; The Small Patent Law Group

(57) ABSTRACT

Methods and systems for automatic patient table positioning are provided. The method includes determining patient specific scan parameters and positioning the patient with the imaging scanner based on the determined patient specific scan parameters.

20 Claims, 3 Drawing Sheets

METHODS AND SYSTEMS FOR AUTOMATIC PATIENT TABLE POSITIONING

CROSS REFERENCE TO RELATED APPLICATIONS

This application claims priority to and the benefit of the filing date of U.S. Provisional Application No. 60/710,393, filed on Aug. 23, 2005, entitled "METHODS AND SYSTEMS FOR AUTOMATIC PATIENT TABLE POSITIONING," which is hereby incorporated by reference in its entirety.

BACKGROUND OF THE INVENTION

This invention relates generally to medical imaging systems and, more particularly, to controls and methods for positioning patients in medical imaging systems.

Medical imaging often requires accurate and repeatable positioning of the patient for a scan. For example, in nuclear tomography, cardiology scanning requires patient positioning such that the heart is as close as possible to the center of rotation (COR) of the camera. This is typically achieved by manually adjusting the table height so that the patient's torso is centered within the COR of the camera. This process requires bending on the part of the operator in order to place the operator's eye in a direct horizontal line with the COR. In addition, the table height used for loading and unloading the patient is determined generically and is not always appropriate for the particular patient.

Nuclear tomography, for example, cardiology imaging uses a comparison of the results of two scans, one acquired with the patient at a rest condition and the other acquired with the patient at a stress condition. For such comparison to be clinically optimal, patient positioning during each scan that may occur hours apart is important.

BRIEF DESCRIPTION OF THE INVENTION

In one embodiment, a method for automatic positioning of a patient within an imaging scanner is provided. The method includes determining patient specific scan parameters and positioning the patient with the imaging scanner based on the determined patient specific scan parameters.

In another embodiment, a method for automatically determining scan parameters for a medical imaging scanner is provided. The method includes accessing one of (i) previous scan parameter information and (ii) demographic data. The method further includes automatically determining the scan parameters based on one of processing of the demographic data and downloading of the previous scan parameter information.

In yet another embodiment, a medical imaging system is provided that includes an imaging portion for imaging a patient and a control portion configured to control the imaging. The control portion is configured to control at least one of a position and scanning of the patient based on patient specific scan parameters.

DETAILED DESCRIPTION OF THE INVENTION

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

Figure 1:
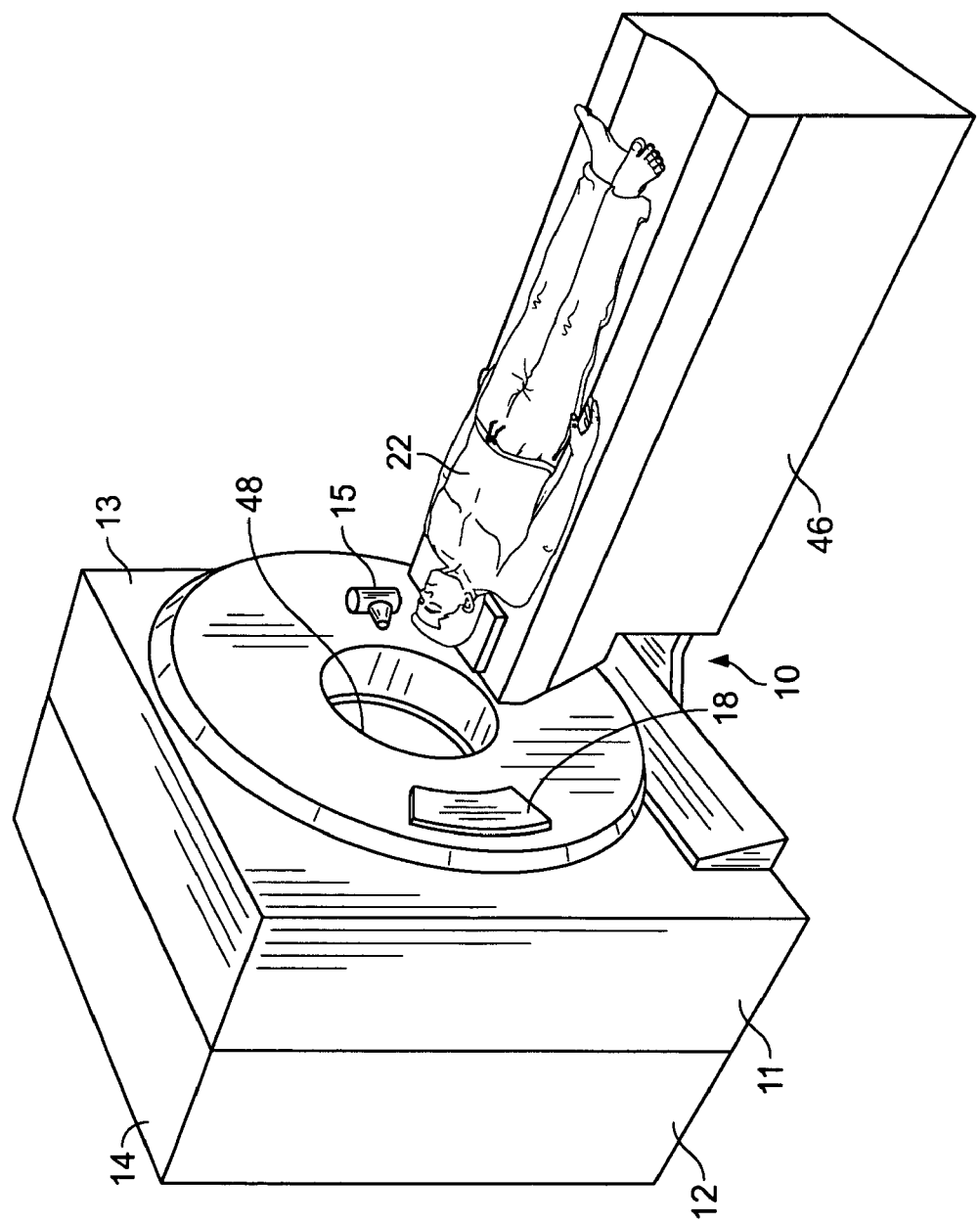
FIG. 1 is a perspective view of an exemplary imaging system.
Figure 2:
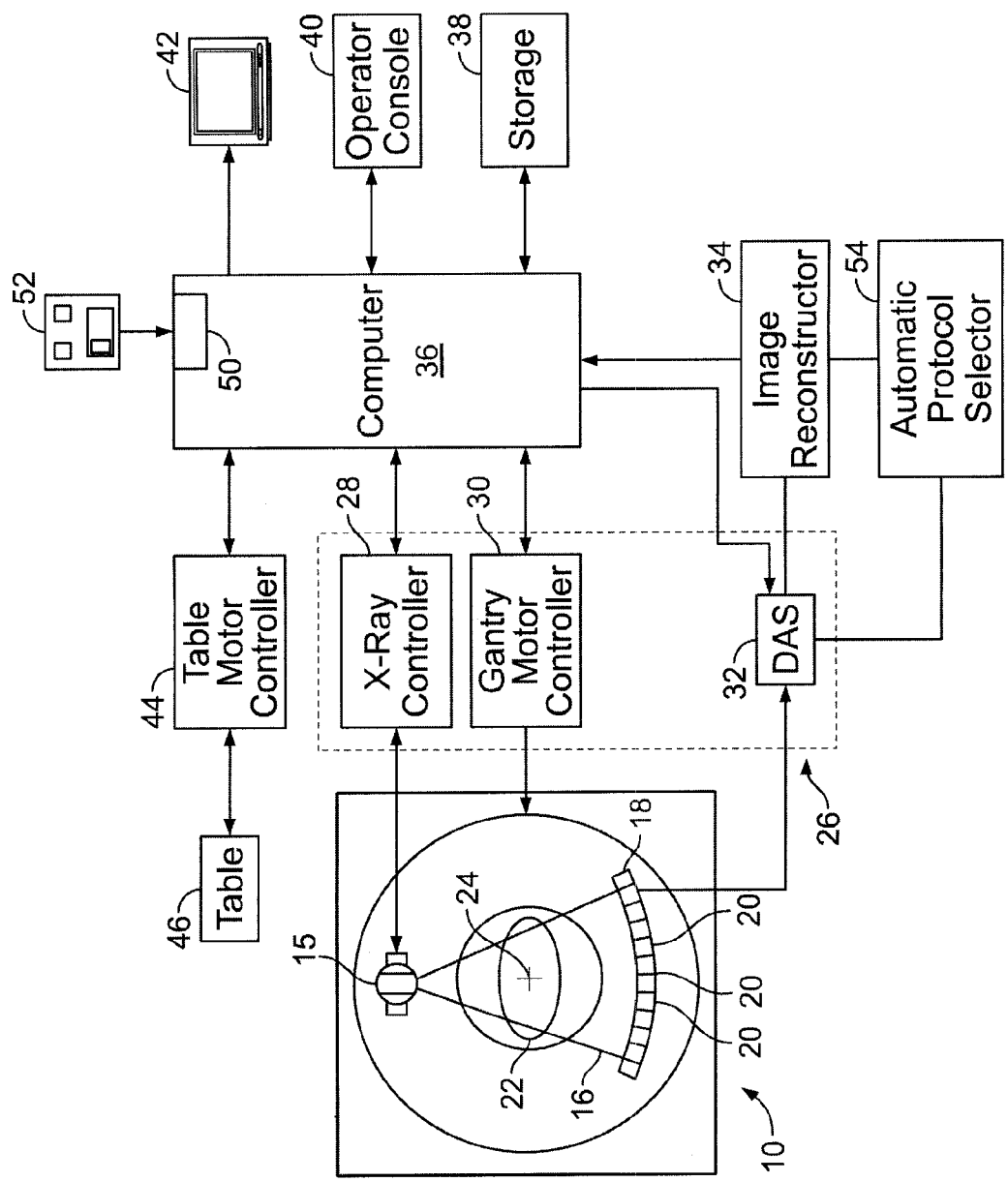
FIG. 2 is a schematic block diagram of the imaging system shown in FIG. 1.

FIG. 1 is a perspective view of an exemplary imaging system 10 constructed in accordance with various embodiments of the invention. FIG. 2 is a schematic block diagram of the imaging system 10 (shown in FIG. 1). In the exemplary embodiment, the imaging system 10 is a multi-modal imaging system and includes a first modality unit 11 and a second modality unit 12. The modality units 11 and 12 enable the system 10 to scan an object, for example, a patient, in a first modality using the first modality unit 11 and to scan the object in a second modality using the second modality unit 12. The system 10 allows for multiple scans in different modalities to facilitate an increased diagnostic capability over single modality systems. In one embodiment, the multi-modal imaging system 10 is a Computed Tomography/Positron Emission Tomography (CT/PET) imaging system 10. The CT/PET system 10 includes a first gantry 13 associated with the first modality unit 11 and a second gantry 14 associated with the second modality unit 12. In alternative embodiments, modalities other than CT and PET may be employed with the imaging system 10. The gantry 13, in an embodiment, includes the first modality unit 11 that has an x-ray source 15 that projects a beam of x-rays 16 toward a detector array 18 on the opposite side of the gantry 13. The detector array 18 is formed by a plurality of detector rows (not shown) including a plurality of detector elements 20 that together sense the projected x-rays that pass through an object, such as a patient 22. Each detector element 20 produces an electrical signal that represents the intensity of an impinging x-ray beam and allows estimation of the attenuation of the beam as the beam passes through the object or patient 22.

In other embodiments, the system 10 includes only a single gantry having a first rotor configured to carry the first modality system and a second rotor configured to carry the second modality system. In various other embodiments the system 10 includes only one modality, such as CT.

During a scan to acquire x-ray projection data the gantry 13 and the components mounted thereon rotate about an examination axis 24. FIG. 2 shows only a single row of detector elements 20 (i.e., a detector row). However, the detector array 18 may be configured as a multislice detector array having a plurality of parallel detector rows of detector elements 20 such that projection data corresponding to a plurality of slices can be acquired simultaneously during a scan. To acquire emission data, the gantry 14 rotates one or more gamma cameras (not shown) about the examination axis 24. The gantry 14 may be configured for continuous rotation during an imaging scan and/or for intermittent rotation between imaging frames.

The rotation of the gantries 13 and 14, and the operation of the x-ray source 15 are controlled by a control mechanism 26 of the system 10 (e.g., CT/PET system). The control mechanism 26 includes an x-ray controller 28 that provides power and timing signals to the x-ray source 15 and a gantry motor controller 30 that controls the rotational speed and position of the gantry 13 and the gantry 14. A data acquisition system (DAS) 32 of the control mechanism 26 samples data from the detector elements 20 and the gamma cameras and conditions the data for subsequent processing. An image reconstructor 34 receives sampled and digitized x-ray data and emission data from the DAS 32 and performs high-speed image reconstruction. The reconstructed image is transmitted as an input to a computer 36 that stores the image in a storage device 38.

The computer 36 also receives commands and scanning parameters from an operator via console 40 that has an input device, such as, a keyboard. An associated display 42 allows the operator to observe the reconstructed image and other data from the computer 36. Operator supplied commands and parameters are used by the computer 36 to provide control signals and information to the DAS 32, the x-ray controller 28 and the gantry motor controller 30. In addition, the computer 36 operates a table motor controller 44 that controls a motorized table 46 to position the patient 22 in the gantry 13 and 14. Specifically, the table 46 moves portions of the patient 22 through the gantry opening 48.

In one embodiment, the computer 36 includes a read/write device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or an other digital source such as a network or the Internet, as well as yet to be developed digital means. In another embodiment, the computer 36 executes instructions stored in firmware (not shown). The computer 36 is programmed to perform functions as described herein, and as used herein, the term computer is not limited to integrated circuits referred to in the art as computers, but broadly refers to computers, processors, microcontrollers, microcomputers, programmable logic controllers, application specific integrated circuits, and other programmable circuits, and these terms are used interchangeably herein. The system 10 may also includes a plurality of other detectors, for example, PET detectors (not shown) including a plurality of detector elements. The PET detectors and the detector array 18 both detect radiation and are both referred to herein as radiation detectors.

An automatic protocol selector 54 is communicatively coupled to the DAS 32 and the image reconstructor 34 to transmit settings and parameters for use by the DAS 32 and the image reconstructor 34 during a scan and/or image reconstruction and image review. Although the automatic protocol selector 54 is illustrated as a separate component, it should be understood that that functions performed by the automatic protocol selector 54 may be incorporated into functions performed by, for example the computer 36. Accordingly, the automatic protocol selector 54 may be embodied in a software code segment executing on a multifunctional processor or may embodied in a combination of hardware and software.

Additionally, although described in a medical setting, it is contemplated that the embodiments of the invention may be implemented in connection with other imaging systems including industrial CT systems such as, for example, but not limited to, a baggage scanning CT system typically used in a transportation center such as, for example, but not limited to, an airport or a rail station, non-destructive testing systems, etc.

Figure 3:
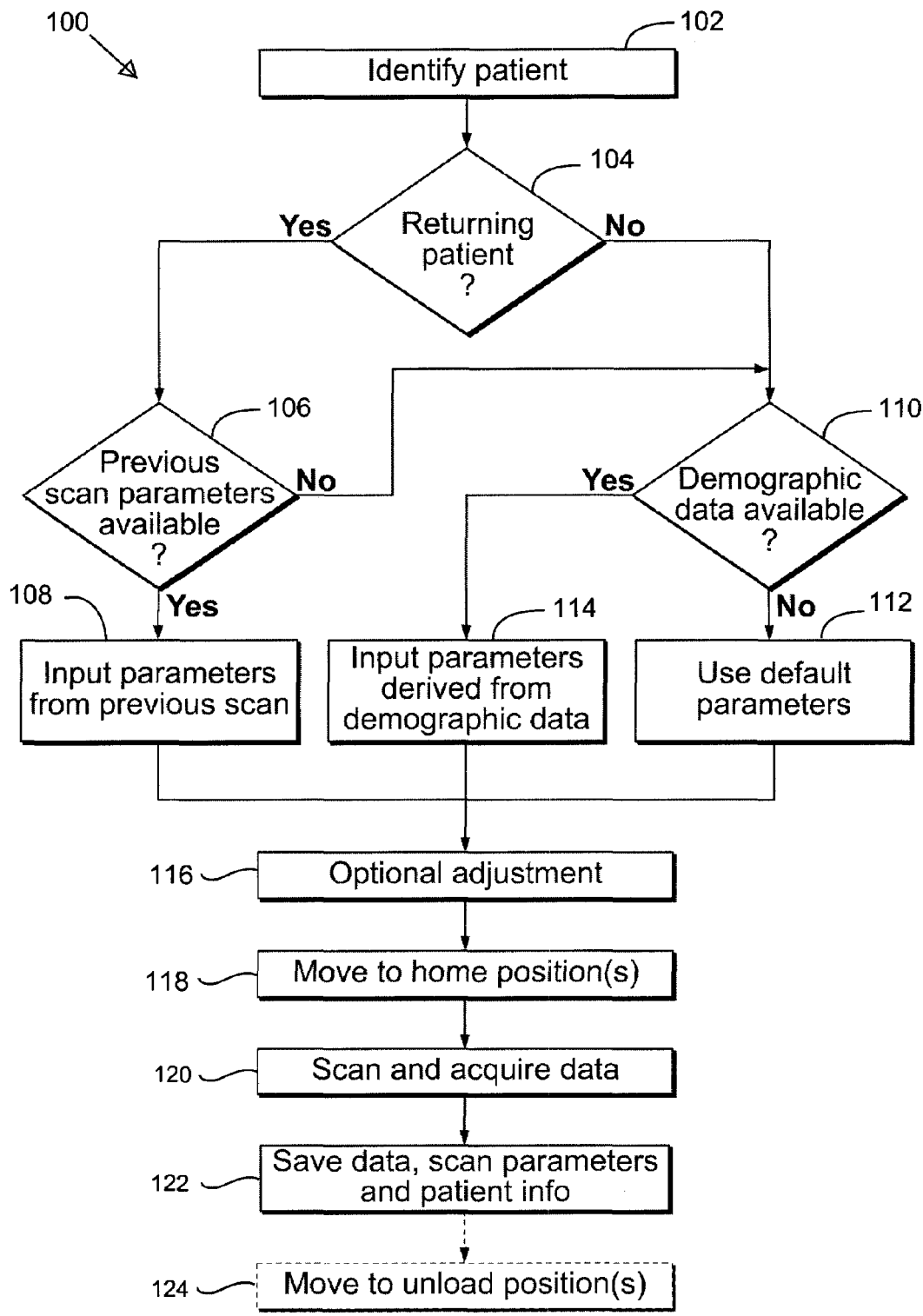
FIG. 3 is a flowchart of an exemplary method of medical imaging using automatic scan parameters in accordance with an embodiment of the present invention.

FIG. 3 is a flowchart of an exemplary method 100 of determining automatic scan parameters for the medical imaging system shown in FIG. 1. The method may be embodied on a computer readable medium, such as programmed instructions in software or firmware configured to control the computer 36 (shown in FIG. 2) to perform the functions described herein and may be implemented using, for example, the X-ray controller 28 and/or the table motor controller 44 (both shown in FIG. 2).

In various exemplary embodiments, depending on the available information, scan parameters are determined in different manners, which may include determining patient specific scan parameters. In general, when no patient specific parameters are available, default values are used. When only demographic information, for example, height, weight, gender, age etc., is available, approximated scan parameters are derived from the demographic information. Derived scan parameters may be based on experience with similar patients or may be learned from an algorithm configured to optimize the scan parameters based on an automatically modified control script. If the patient has already been scanned on the particular system or another camera of the same or similar type, scan parameters from a previous scan are used.

It should be noted that in the various exemplary embodiments, scan parameters include, but are not limited to:

1. A "Load" position that generally defines a patient loading position, for example, positioning the table to ease a patient climbing onto table.
2. An "Unload" position that generally defines a patient unloading position, for example, positioning the table to ease patient climbing off the table at the end of a scan. In some cases, the load and unload positions may be substantially the same.
3. A "Home" position defining a configuration at a scan start including, for example, a table in/out position, a table up/down (height) position, a table left/right position, and a radial position of the detector. Additional scan parameters at the scan start also may be configured in the home position, such as, an incline of the table and/or gantry, and a detector rotation position that is typically determined by the type of study (and is patient independent).

More particularly, the method 100, which may be provided as an automatic scan parameter algorithm, includes identifying a patient at 102. For example, patient data, which may initially include, for example, a patient name, birth date and/or other identifier, are entered into the system (e.g., medical imaging system). A determination is then made at 104 as to whether the patient identified by the inputted information is a returning patient. This may include, for example, searching a database of patients, which may be provided as part of the information stored in the medical database of a hospital or clinic. If it is determined that the patient is a returning patient at 104, then additional identification information (e.g., address and phone number) need not be entered, but may be updated. Thereafter, a determination is made at 106 as to whether previous scan parameters are available for the identified returning patient. If a determination is made at 106 that previous scan parameters are available for the patient, then at 108 the scan parameters are input in the system, which may be automatically downloaded or manually input from, for example, a print out. For example, for automatic positioning for subsequent scans of the same patient, actual setup settings may be saved that specify physical positioning (e.g. table height, table in/out, detector radius, start angle) and accessed for reuse for subsequent scans of the same patient. Once the scan parameters are input or downloaded, a user may optionally adjust the parameters at 116, for example, based on the scan to be performed, a change in weight of the patient, etc. Thereafter, an initialization process may be initiated, for example, with the table of the medical scanner moving to a load position. When the patient is positioned on the table, the medical scanner then may be moved to a scan position, for example, moved to a home position at 118. Thereafter, at 120 a scan is performed and scan data is acquired in any known manner. Additionally, the scan data, scan parameters and/or patient information may be stored at 122. Once the scan is complete, the system may move the table to an unload position at 124 allowing a patient to be removed from the scanner.

If at 104, a determination is made that the patient is not a returning patient, or if at 106 a determination is made that there are no previous scan parameters for a returning patient, then at 110 a determination is made as to whether demographic data is available. If at 110 a determination is made that no demographic data is available then at 112 default scan parameters are used. For example, default scan parameters for a load, unload and home position for the particular medical imaging scanner (e.g., factory default settings, doctor default settings, etc.) may be used to set up and perform the scan, which is performed at 116, 118, 120, 122 and 124 as described in more detail herein.

If at 110 a determination is made that demographic data is available then at 114 input scan parameters are derived from the demographic data, for example, as stored in the medical imaging system. For example, in an exemplary embodiment, an operator initiated initial automated motion may be provided that brings the table of the imaging scanner into a bore of the imaging scanner and up to an approximate height determined according to the patient demographics. The patient demographics may be entered by the patient or a user or may optionally be provided by a Health Information Service/Radiology Information System (HIS/RIS) or Picture Archive and Communications System (PACS) system such that the user does not need to enter this information. Patient weight and height may be used to calculate a patient Body Mass Index (BMI) value in any known manner, for example, using the following equation: Body Weight (in kilograms)/ Height$^2$(meters). This value is then used to calculate the chest depth in order to determine the optimal table height for this patient. These and additional patient demographics (e.g. gender, ethnicity) are used to calculate the optimal positioning for scanning as well as the patient loading and unloading height, for example, to set the load, unload and home positions. Thereafter, a setup and scan procedure may be performed at 116, 118, 120, 122 and 124 as described in more detail herein.

Automatic scan parameters associated with medical imaging systems provide consistent patient positioning for a subsequent scans using previous scan parameters stored in memory and/or demographic information. Using automatic scan parameters reduces scan time by automating table motion, which centers the patient within the Center of Rotation (COR) of the camera bore, reduces errors, and facilitates improving image consistency such that images can be compared without errors related to inconsistent positioning. Various embodiments may provide an automatic scan parameter algorithm configured to learn various parameters, in particular positioning settings from actual values used in previous scans for the same patient. The table motion is personalized for loading and unloading reducing patient anxiety.

Although various embodiments are described above relative to a nuclear medicine system, other medical imaging modalities, such as computed tomography (CT), single positron emission tomography (SPECT), positron emission tomography (PET), nuclear magnetic resonance imaging (MRI), static X-ray imaging, dynamic (Fluoroscopy) X-ray imaging, and multimodality combinations thereof may also benefit form the methods described herein and the use of various embodiments of the present invention are contemplated with respect to these modalities.

The above-described embodiments of a medical imaging system provide a cost-effective and reliable means for using automatic scan parameters to control default positioning of the patient determined by previous scans or patient demographics and providing automatic positioning of the patient during the scan and subsequent scans of the same patient.

Exemplary embodiments of medical imaging systems and apparatus are described above in detail. The medical imaging system components illustrated are not limited to the specific embodiments described herein, but rather, components of each system may be utilized independently and separately from other components described herein. For example, the medical imaging system components described above may also be used in combination with different medical imaging system components.

A technical effect of the various embodiments of the systems and methods described herein include facilitating operation of the medical imaging system by providing personalization of the automated table positioning. Specifically, the methods permit the operator to efficiently move the table to a position that is appropriate for the patient and avoid multiple manual adjustment operations.

While the invention has been described in terms of various specific embodiments, those skilled in the art will recognize that the various embodiments of the invention can be practiced with modification within the spirit and scope of the claims.

What is claim is:

1. A method for automatic positioning of a patient within an imaging scanner, said method comprising:
    determining patient specific scan parameters, wherein the determined patient specific scan parameters include a determined position of at least one of a patient table and the imaging scanner, and wherein determining the determined position comprises at least one of:
        using a previous position from a previous scan of the patient as the determined position; and
        using patient demographic information; and
    positioning the patient with the imaging scanner based on the determined patient specific scan parameters.

2. A method in accordance with claim 1 wherein the determining patient specific scan parameters comprises using scan parameters from a previous scan of the patient to determine the scan parameters.

3. A method in accordance with claim 1 wherein the determining patient specific scan parameters comprises using patient demographic information to determine the scan parameters.

4. A method in accordance with claim 3 wherein the patient demographic information comprises at least one of gender and ethnicity.

5. A method in accordance with claim 1 wherein the determining patient specific scan parameters comprises calculating a Body Mass Index (BMI) value based on a weight and height of the patient.

6. A method in accordance with claim 1 further comprising determining a table height for positioning a patient within the imaging scanner based on a chest depth of the patient.

7. A method in accordance with claim 1 wherein the determining patient specific scan parameters comprises using patient demographic information from one of a HIS/RIS and PACS system.

8. A method in accordance with claim 1 wherein the determined position comprises at least one of a load position, an unload position and a home position for scanning the patient based on the patient specific scan parameters.

9. A method in accordance with claim 1 further comprising acquiring information from one of (i) a medical imaging system and (ii) a user input, to determine the patient specific scan parameters.

10. A method in accordance with claim 1 further comprising storing the determined patient specific scan parameters in a medical imaging system.

11. A method in accordance with claim 1 further comprising identifying the patient based on patient information.

12. A method in accordance with claim 11 further comprising determining whether the patient is a returning patient based on the patient information and, if available, using previous patient specific scan parameters for the returning patient.

13. A method in accordance with claim 12 further comprising using demographic data if previous patient specific scan parameters for the returning patient are not available.

14. A method in accordance with claim 1 wherein the positioning comprises one of (i) automatically moving the patient table with the patient thereon to a position within the imaging scanner and (ii) automatically controlling movement of the imaging scanner to scan the patient, based on the determined patient specific scan parameters.

15. A method in accordance with claim 1, wherein the determined position includes at least one of a relative location between the patient table and the imaging scanner and a relative orientation between the patient table and the imaging scanner.

16. A method for automatically determining scan parameters for a medical imaging scanner, said method comprising:
accessing one of (i) positional information about a previous position of at least one of a patient table and the imaging scanner from a previous scan of the patient and (ii) demographic data;
automatically determining the scan parameters based on one of processing of the demographic data and downloading of the previous position, wherein the determined scan parameters include a determined position of at least one of the patient table and the imaging scanner; and
at least one of storing the determined scan parameters, positioning a patient based on the determined scan parameters, and scanning the patient based on the determined scan parameters.

17. A method in accordance with claim 16 wherein the processing comprises determining a Body Mass Index (BMI) of a patient based on a weight and height of the patient.

18. A method in accordance with claim 16 further comprising one of positioning and scanning a patient based on the determined scan parameters and wherein a user input provides a further adjustment to the positioning.

19. A method in accordance with claim 16 further comprising storing the determined scan parameters as patient specific scan parameters.

20. A medical imaging system comprising:
an imaging portion for imaging a patient; and
a control portion configured to control the imaging, the control portion configured to control at least one of a position and scanning of the patient based on patient specific scan parameters, wherein the patient specific scan parameters include a determined position of at least one of a patient table and the imaging portion, and wherein determining the determined position comprises at least one of:
using a previous position from a previous scan of the patient as the determined position; and
using patient demographic information.

* * * * *